US011376201B2

(12) United States Patent
Winn

(10) Patent No.: US 11,376,201 B2
(45) Date of Patent: *Jul. 5, 2022

(54) MICELLAR EXTENDED RELEASE NANOSTRUCTURES

(71) Applicant: Craft Packaging LLC, Draper, UT (US)

(72) Inventor: Travis Winn, Draper, UT (US)

(73) Assignee: Craft Packaging, LLC, Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/021,299

(22) Filed: Sep. 15, 2020

(65) Prior Publication Data

US 2021/0000717 A1    Jan. 7, 2021

Related U.S. Application Data

(63) Continuation of application No. 16/381,331, filed on Apr. 11, 2019.

(60) Provisional application No. 62/782,288, filed on Dec. 19, 2018.

(51) Int. Cl.

| | | |
|---|---|---|
| *G01N 27/02* | (2006.01) | |
| *A61K 8/00* | (2006.01) | |
| *A61K 8/36* | (2006.01) | |
| *A61K 8/02* | (2006.01) | |
| *A61Q 13/00* | (2006.01) | |
| *C11B 9/00* | (2006.01) | |
| *A61K 8/11* | (2006.01) | |
| *A61K 8/81* | (2006.01) | |
| *A61K 36/889* | (2006.01) | |
| *A61L 9/14* | (2006.01) | |
| *A61Q 15/00* | (2006.01) | |

(52) U.S. Cl.
CPC ............ *A61K 8/361* (2013.01); *A61K 8/0291* (2013.01); *A61K 8/11* (2013.01); *A61K 8/8152* (2013.01); *A61K 36/889* (2013.01); *A61L 9/14* (2013.01); *A61Q 13/00* (2013.01); *A61Q 15/00* (2013.01); *C11B 9/0011* (2013.01); *C11B 9/0015* (2013.01); *C11B 9/0019* (2013.01); *C11B 9/0034* (2013.01); *C11B 9/0049* (2013.01); *A61K 2800/412* (2013.01); *A61K 2800/56* (2013.01); *A61K 2800/62* (2013.01); *A61K 2800/654* (2013.01)

(58) Field of Classification Search
CPC .......... A61K 36/889; A61K 8/35; A61K 8/11; A61K 8/37; A61K 8/347; A61K 8/361; A61K 8/8152; A61K 8/34; A61K 8/0291; A61K 2800/654; A61K 2800/56; A61K 2800/30; A61K 2800/5922; A61K 2800/412; A61K 2800/62; A61L 9/14; A61Q 15/00; A61Q 13/00
USPC .................................. 424/76.2, 76.1; 512/1
See application file for complete search history.

(56) References Cited

U.S. PATENT DOCUMENTS

| | | | |
|---|---|---|---|
| 10,617,614 B1* | 4/2020 | Winn | .................... A61K 8/0291 |
| 2008/0069785 A1* | 3/2008 | Jones | ....................... A61K 8/35 |
| | | | 424/59 |

* cited by examiner

*Primary Examiner* — Jessica Whiteley
(74) *Attorney, Agent, or Firm* — Loyal IP Law, PLLC; Travis Banta

(57) ABSTRACT

Compositions and methods of manufacture for an extended time-release fragrance comprising volatile organic compounds. A composition of the disclosure includes an effective amount of a volatile organic compound for providing a fragrance that can be sensed by a user and fractionated coconut oil comprising caprylic acid and capric acid.

10 Claims, 6 Drawing Sheets

MICELLAR EXTENDED RELEASE NANOSTRUCTURES

CROSS-REFERENCE TO RELATED APPLICATIONS

This application is a continuation of U.S. patent application Ser. No. 16/381,331, filed on Apr. 11, 2019, and claims the benefit and priority of U.S. patent application Ser. No. 16/381,331 and, thereby, claims the benefit and priority of U.S. Provisional Application No. 62/782,288, filed Dec. 19, 2018, entitled "A Fragrance Composition" which are incorporated herein by reference in their respective entireties, including but not limited to those portions that specifically appear hereinafter, the incorporation by reference being made with the following exception: In the event that any portion of the above-referenced provisional application is inconsistent with this application, this application supersedes said above-referenced provisional application.

TECHNICAL FIELD

The disclosure relates generally to a composition of matter. The composition further relates to fragrances, particularly compositions related to fragrance bases.

BACKGROUND

The sense of smell may be the most underutilized and least understood of the human senses. The sense of smell (referred to as olfaction) operates by the use of odorant receptor cells in the body. These odorant receptor cells help the body sense and process different smells. The brain can process conscious and unconscious odorant molecules that prompt different reactions by the body. Many fragrances are designed to include odorant molecules that will be processed by the body both consciously and unconsciously.

The sense of smell can be a very powerful sense that can have psychological and physiological impacts on a body. Smells can incite memories, impact emotions, increase motivation, lower stress, stimulate self-confidence, and more. Some fragrances seek to capitalize on the powers of smell by creating unique blends of scents that can be applied to a person's body, clothes, surroundings, and so forth.

Fragrances and perfumes have existed for thousands of years. Bottles of fragrance have been uncovered that date back to ancient Egypt and India. Throughout the $16^{th}$ century, Europe and particularly France experienced a rise in the popularity of fragrances. Fragrances were frequently applied to furniture, gloves, clothing, hair, and a person's body. The fragrance industry continues to grow and includes the production of perfumes, mists, aftershaves, body rubs, air fresheners, and others. Fragrances provide numerous benefits and represent and important aspect of a person's everyday life.

Traditionally, fragrances and other compositions that include volatile organic compounds are manufactured with an alcohol or ethanol solvent. The alcohol or ethanol solvent can enable the fragrance or other volatile organic compound to be solubilized in a solvent. However, alcohol and ethanol are undesirable for many users and can cause unpleasant side effects for a user. For example, applying alcohol or ethanol to skin causes the skin to become dehydrated, can cause damage to layers of the skin, and can cause painful or irritating rashes on the skin. Additionally, fragrances or other volatile organic compounds that are solubilized in an alcohol or ethanol solvent can cause headaches or migraines for some users.

Additionally, alcohol and ethanol solutions can evaporate very quickly at ambient conditions. When a fragrance having an alcohol or ethanol base is applied or sprayed, the alcohol or ethanol will quickly evaporate and cause the fragrant molecules to quickly dissipate. When the fragrant molecules have dissipated, a user can no longer sense the fragrance and the fragrance must be reapplied.

Additionally, alcohol and ethanol solutions are known to kill or harm beneficial bacteria on a user's skin. This beneficial bacteria may be known as the "microbiome" of the user's skin and can provide numerous health benefits including fighting off pathogenic bacteria and preventing the user from becoming sick. The microbiome of the skin is vital for skin health and also for overall health by supporting the user's immune system.

In light of the foregoing, disclosed herein are compositions and methods of manufacture for gentle fragrance solutions having extended time-release attributes.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Figure 1A:
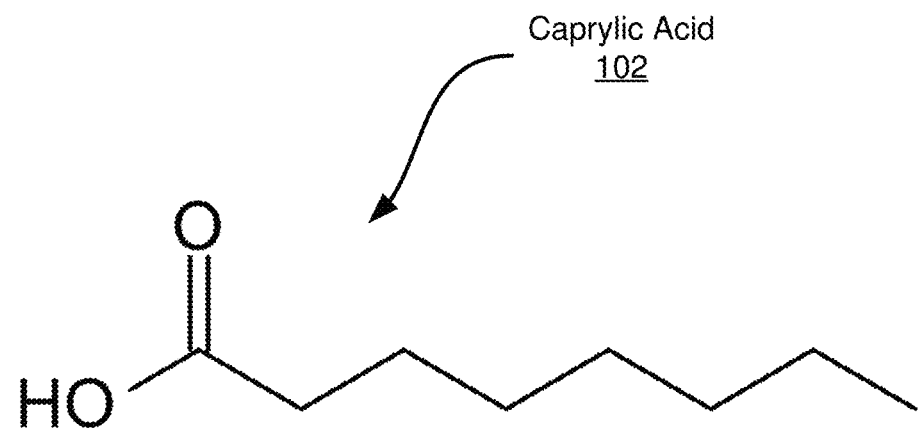
FIG. 1A is the chemical structure of caprylic acid.

Disclosed herein are micellar extended release nanostructures and systems and methods for preparing the same. An embodiment of the micellar extended release nanostructures are derived from a compositional mixture of fractionated coconut oil and volatile organic compounds. Embodiments of the micellar nanostructure compositions provide a gentle fragrance solution that can be applied topically to a user without causing adverse skin reactions such as skin dehydration, skin irritation, or skin damage. Additionally, embodiments of the micellar nanostructure compositions provide an extended time-release of volatile organic compounds such that the compositions are longer lasting at least when compared with alcohol-based compositions.

In an embodiment, a composition is provided as a gentle and extended time-release fragrance. The composition includes an effective amount of a volatile organic compound for providing a fragrance that can be sensed by a user. The composition further includes fractionated coconut oil comprising caprylic acid and capric acid.

An embodiment includes a compositional mixture of fractionated coconut oil and one or more volatile organic compounds. In the compositional mixture, a microemulsion occurs between fatty acids in the fractionated coconut oil and the one or more volatile organic compounds. The compositional mixture provides a means for extended release of the one or more volatile organic compounds.

Embodiments of the compositional mixture may be implemented as fragrances that can be used in perfumes, body products, hair products, cleaning products, air fresheners, and others. Fragrances produced according to the disclosures herein have extended release properties such that the fragrance will last a longer period of time and does not need to be applied as frequently. Additionally, fragrances produced according to the disclosures herein are safe for topical application and are unlikely to cause adverse reactions for a user such as skin irritations or discomfort.

The sense of smell functions by way of odorant receptor cells in the body. The odorant receptor cells belong to a class of proteins known as G protein-coupled receptors (GPCR). Small odorant molecules bind to the receptors of the olfactory system in the upper portion of the nasal epithelium of the body. Electric impulses in the body are sent from the receptors to microdomains called glomeruli. At the glomeruli, the impulses are amplified and then sent to the brain where the scent is perceived and "decoded" by the brain. The brain causes the individual to recognize and "sense" the smell. For many humans, the olfactory system aids the body in accurately discerning over 10,000 different odors. Odorant molecules are one class of a group of organic compounds called volatile organic compounds (VOCs) that are processed by the brain and consciously perceived by the individual.

In addition to the thousands of odorant VOC molecules the brain uses to generate specific odor senses that the individual can consciously recognize, there are also many VOC molecules that may prompt the brain to cause unconscious cognitive and/or physiological changes in the body. The VOCs that cause an unconscious reaction also bind to receptors in the olfactory system. These VOCs may bind to different G protein-coupled receptors in the nasal epithelium or receptors in the vomeronasal organ. The group of VOCs that cause unconscious reactions in the body may also be referred to as pheromones.

Conscious and unconscious reactions to volatile organic compounds have been used in human culture for many years. Fragrances that include volatile organic compounds have been used in communication, attraction, signaling warning, religious ceremonies, and others. Additionally, odor-evoked memories have been shown to have significant implications on physiological and psychological health. Fragrances that include VOCs causing a conscious or unconscious reaction may improve mood, increase motivation, lower stress, stimulate self-confidence, lower inflammation in the body, and others.

Fragrances that may be used in perfumes, body products, makeup products, hair products, air fresheners, and others may combine voltaic organic compounds from plants and other sources. The art and science of mixing fragrances has been occurring for thousands of years. Fragrances are used in many consumer markets, including the perfume industry, the beauty industry, the pharmaceutical industry, the cleaning product industry, and others.

Traditional methods of producing fragrances, perfumes, and other scented products often consists of combining ethanol and/or isopropyl alcohol with an organic-based bioactive compound in an effort to make the formulation water soluble. In many implementations, ethanol and/or isopropyl alcohol is an undesirable solvent for a fragrance. Alcohol-based solvents cause dehydration of the user's skin and damage to the microbiome of the user's skin. Many users experience allergic reactions to alcohol-based solvents and formulations. Alcohol-based formulations are costly to produce and are often regulated by government or other regulatory agencies. Additionally, alcohol-based fragrances are volatile such that the fragrance readily evaporates and requires continued reapplication to maintain effective concentrations of the scent-inducing volatile organic compounds.

Fragrances or other products having an alcohol or ethanol base can be extremely dehydrating when applied to a user's skin. Alcohol and ethanol based solvents strip water molecules off of a user's skin and cause the user to experience an irritation sensation of skin dehydration. Additionally, a significant number of humans experience an allergic reaction when alcohol or ethanol is topically applied to the user's skin. Alcohols and ethanol can irritate skin and cause discomfort ranging from mild tenderness to extensive rashes and boils all over the user's body.

Additionally, hundreds of beneficial species of bacteria live on skin that are vital for the user's health. This collection of bacteria may be referred to as the "microbiome." Beneficial bacterial species living on a user's skin are known to inhibit growth of pathogenic bacteria that is undesirable and can be harmful to the user. Ethanol and alcohol and well known for antibacterial effects and can damage, disturb, or even kill beneficial healthy bacteria living on the surface of a user's skin. When the beneficial healthy bacteria is killed or damage, the user is more susceptible to experiencing an infection or illness caused by pathogenic bacteria.

Additionally, traditional alcohol and/or ethanol based fragrances readily diffuse off the skin and have no extended release effects. Alcohol and ethanol have low boiling points and therefore evaporate quickly at ambient conditions. When the alcohol or ethanol base of a fragrance has evaporated, the volatile organic compounds of the fragrance are emitted into the air and quickly dissipate. When the fragrance molecules have dissipated, users can no longer sense the smell of the fragrance and the fragrance must be reapplied.

Alcohols are regulated by many government agencies and other agencies. As such, it can be prohibitively expensive to manufacture products having an alcohol base.

It is therefore desirable to produce volatile organic compound compositions that do not include an alcohol or ethanol base. It is desirable to provide fragrance compositions that are safe for topical application and do not cause skin dehydration or other skin irritations. Additionally, it is desirable to produce volatile organic compound compositions with an extended release that are not prone to quick evaporation. Disclosed herein are compositions and methods of manufacture for extended release and biosafe mixtures including volatile organic compounds. Such mixtures may be implemented as fragrances, pharmaceuticals, pheromones, and others.

The compositions disclosed herein are not dehydrating for a user's skin and instead provide significant hydration to the user's skin. Fractionated coconut oil in particular is shown to provide unexpectedly good results in hydrating a user's skin and providing relief for skin dehydration or skin irritations. This feature of fractionated coconut oil is due to short chain caprylic acid and capric acid fatty acid chains. These fatty acid chains sit on the surface of the user's skin and form a bilayer were water molecules are captured and retained on the skin. This increases the moisture content of the skin and provides a pleasant hydrated sensation for the user.

Additionally, fractionated coconut oil has no known skin allergenicity and is shown to exert anti-inflammatory effects on a user's skin. This is highly desirable especially when compared against alcohol or ethanol, which are both known for causing allergic reactions and causing various skin irritations.

Further, the short chain fatty acids in fractionated coconut oil such as caprylic acid and capric acid are known to encourage beneficial bacteria grown on a user's skin. The novel composition disclosed herein including fractionated coconut oil and a volatile organic compound is shown to provide prebiotic benefits to the user's skin. The prebiotic benefits cause beneficial bacteria to grow on the user's skin and further combat the growth of pathogenic bacteria that might be harmful or dangerous for the user.

Additionally, the compositions disclosed herein provide unexpectedly good results for providing an extended time-release effect for fragrance molecules or other volatile organic compounds. Specifically, when compared with alcohol or ethanol fragrances, the compositions disclosed herein last five times longer and do not require frequent reapplication. A clinical study disclosed herein (see e.g. FIG. 4) shows that the compositions disclosed herein that include fractionated coconut oil last five times longer than alcohol-based fragrances. This significantly lowers the amount of fragrance that needs to be applied and reduces the cost for a user wishing to use the fragrance.

An embodiment of the disclosure includes fractionated coconut oil and one or more volatile organic compounds. In an embodiment, the fractionated coconut oil is composed almost exclusively of caprylic acid and capric acid. The fractionated coconut oil may include a small amount of caproic acid, lauric acid, and/or myristic acid. The fractionated coconut oil may be selectively enriched in caprylic acid. An embodiment of the one or more volatile organic compounds may include molecules with a molecular weight ranging from 20 g/mol to 700 g/mol. Some example classes of volatile organic molecules include terpenes, flavonoids, alkaloids, polyphenols, flavanols, aporphines, steroids, long-chain hydrocarbons, fullerenes, aromatics, and others. In an embodiment, the fractionated coconut oil is enriched with caprylic acid and exists in the composition in a range from about 10% to about 90% by weight. In an embodiment, the one or more volatile organic compounds exist in the composition in a range from about 0.5% to about 90% by weight.

In the composition, the caprylic acid and the capric acid of the fractionated coconut oil from an electrostatic micellar nanostructure that encapsulate a volatile organic molecule. This causes the volatile organic molecule to have a slow release. In the case of a fragrance, this extends the time the fragrance releases volatile organic molecules and gives off a scent.

An embodiment is implemented as an extended time release fragrance. The extended time release fragrance could be implemented in a perfume, hair product, soap, lotion, serum, cleanser, emulsion, air freshener, candle, skin product, makeup product, and others. The composition disclosed herein provides unexpectedly good results for releasing a fragrance slowly over time. When the fragrance is released slowly over time, the composition will provide the intended scent for a longer period of time and therefore will not need to be applied as frequently.

An embodiment is implemented as an extended release pharmaceutical or biological compound. The pharmaceutical or biological compound may be particularly suited for instances where time released capability or slow release capability is needed or beneficial. Example pharmaceutical compositions that benefit from time release include anti-seizure medications, extended release insulin, anti-depression medications, and others. The composition disclosed herein is safe and can be ingested and may therefore provide a benign means to provide a slow release of a pharmaceutical or biological compound. This can improve the effectiveness of the pharmaceutical and enable the pharmaceutical to achieve its intended purpose.

An embodiment is implemented as an extended release insect repellant. The extended release insect repellant may be implemented as a topical formulation or a formulation that is intended to be diffused without being applied to skin, clothing, or other substances. When the insect repellant is encapsulated with the fractionated coconut oil as disclosed herein, the scent of the insect repellant is released slowly over time. This causes the insect repellant to be effective for a longer period of time, so it does not need to be applied as frequently. Additionally, the fractionated coconut oil compositions disclosed herein may be safer for topical applications for many users and may reduce the likelihood of skin irritation that is common with insect repellants.

An embodiment is implemented as a pheromone formulation. A pheromone formulation may emit one or more pheromones to capitalize on unconscious reception of molecules by the olfactory system. An example implementation of a pheromone formulation may cause a person to be drawn or attracted to another individual based on the pheromone scents that are unconsciously sensed by the person's olfactory system. When the pheromone is encapsulated in the fractionated coconut oil composition as disclosed herein, the pheromone scent is released slowly over time and therefore lasts longer and does not need to be applied as frequently.

An embodiment is implemented as an extended release of any suitable volatile organic compound. Example volatile organic compounds that may be useful may be implemented in clothing, dryer balls, masks, and others. In an implementation, a dryer ball or other object is infused with the volatile organic compound fractionated coconut oil composition as disclosed herein. The dryer ball may slowly release the volatile organic compounds over time during use.

An embodiment is implemented as a perfume, hair product, body product, or makeup product with a base comprising fractioned coconut oil. The product may include fractionated coconut oil in place of an alcohol base as commonly used in perfumes and other beauty or fragrance products. The fractionated coconut oil base increases the likelihood that a user will not have an adverse reaction to the product such as skin irritation or skin dehydration. The fractionated coconut oil base hydrates the user's skin and is safe and pleasant for the user.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Before the structure, systems, methods, and compositions for micellar extended release nanostructures are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified ingredients, materials or steps and those that do not materially affect the basic and novel characteristic or characteristics of the claimed disclosure.

As used herein, "effective amount" means an amount of an ingredient or a component of the product that is nontoxic, but sufficient to provide the desired effect and performance at a reasonable benefit/risk ratio attending any dietary supplement or product. For example, an effective amount of a vitamin or mineral is an amount sufficient to prevent a deficiency thereof and to reduce the incidence of some adverse effects.

Unless defined otherwise, all technical and scientific terms used herein have the same meanings as commonly understood by one of ordinary skill in the art to which this disclosure pertains and belongs.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1B:
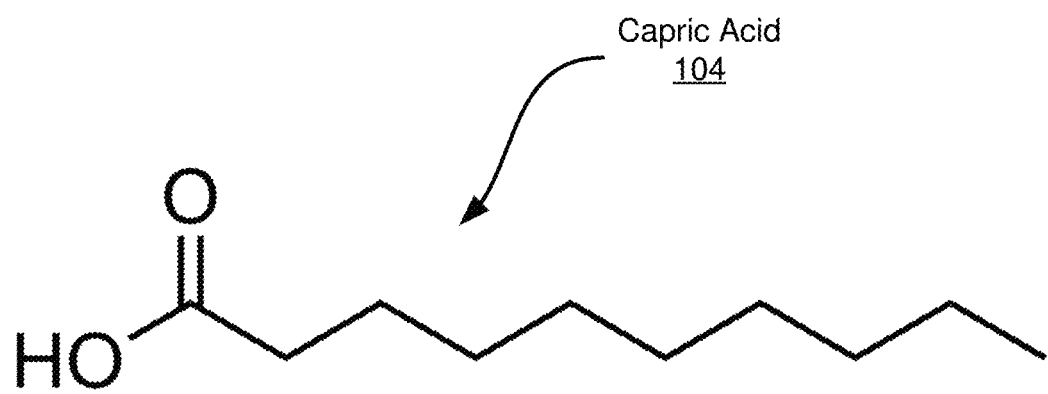
FIG. 1B is the chemical structure of capric acid.

Referring now to the figures, FIG. 1 illustrates the chemical structures of caprylic acid 102 and capric acid 104. The compositions disclosed herein may include fractionated coconut oil including a high proportion of caprylic acid 102 and/or capric acid 104.

Caprylic acid 102 is the common name for an eight-carbon fatty acid known by the systematic name octanoic acid. Caprylic acid 102 is a medium-chain saturated fatty acid having the chemical formula $CH_3(CH_2)_6COOH$. Caprylic acid 102 is found in coconut oil and other substances such as palm kernel oil and milk from various mammals. In its liquid form, caprylic acid 102 is oily and is minimally soluble in water. The natural form of caprylic acid 102 causes many individuals to experience a slightly unpleasant rancid-like smell and taste.

Capric acid 104 is the common name for a ten-carbon fatty acid known by the systematic name decanoic acid. Capric acid 104 is a saturated fatty acid having the chemical formula $CH_3(CH_2)_8COOH$. Capric acid 104 occurs naturally in coconut oil, palm kernel oil, milk from various mammals, and animal fats.

The composition disclosed herein may use fractionated coconut oil that is produced by one or more different methods. Coconut oil can be produced by a dry process, a wet process, may be refined, may be hydrogenated, and may be fractionated. Coconut oil may be fractionated such that different saturated fats are separated. In an embodiment, the composition includes fractionated coconut oil having a higher content caprylic acid 102 and/or capric acid 104.

Fractionation of coconut oil is a separation process in which certain components are separated. Fractionation can include separating a certain quantity of a component during a phase transition. Fractions of the whole (e.g. different fatty acids within coconut oil) may be collected based on differences in a specific property of the individual components. Liquid substances can be fractionated by way of fractional distillation based on differences in boiling point. Fractionation can be implemented in column chromatography based on differences in affinity between stationary phase and mobile phase. Additional implementations of fractionation include fractional crystallization, fractional freezing, and fractionation based on solubility at given temperatures.

An embodiment of the fractionated coconut oil as used herein is predominantly a mixture of caprylic acid 102 and capric acid 104. Lauric acid and other higher molecular weight fatty acids may be entirely or mostly removed by way of fractionation. The percentage of caprylic acid 102 in the fractionated coconut oil may range from about 30% to about 80% in some embodiments. The percentage of capric acid 104 in the fractionated coconut oil may range from about 10% to about 60%. The fractionated coconut oil used herein that comprises primarily caprylic acid 102 and capric acid 104 may be odorless and translucent.

An embodiment of the composition disclosed herein includes fractionated coconut oil and one or more volatile organic compounds. The composition may be delivered as a fragrance and used in, for example, perfumes, body products such as lotions or ointments, hair products such as shampoos or sprays, makeups, and others. The caprylic acid 102 and the capric acid 104 in the fractionated coconut oil support the formation of unique nanostructures that deliver an extended time release of the one or more volatile organic compounds. Therefore, the one or more volatile organic compounds are slowly released over time and the composition is more effective and longer lasting for delivering a fragrance when compared with traditional fragrances having an alcohol base.

Figure 2:
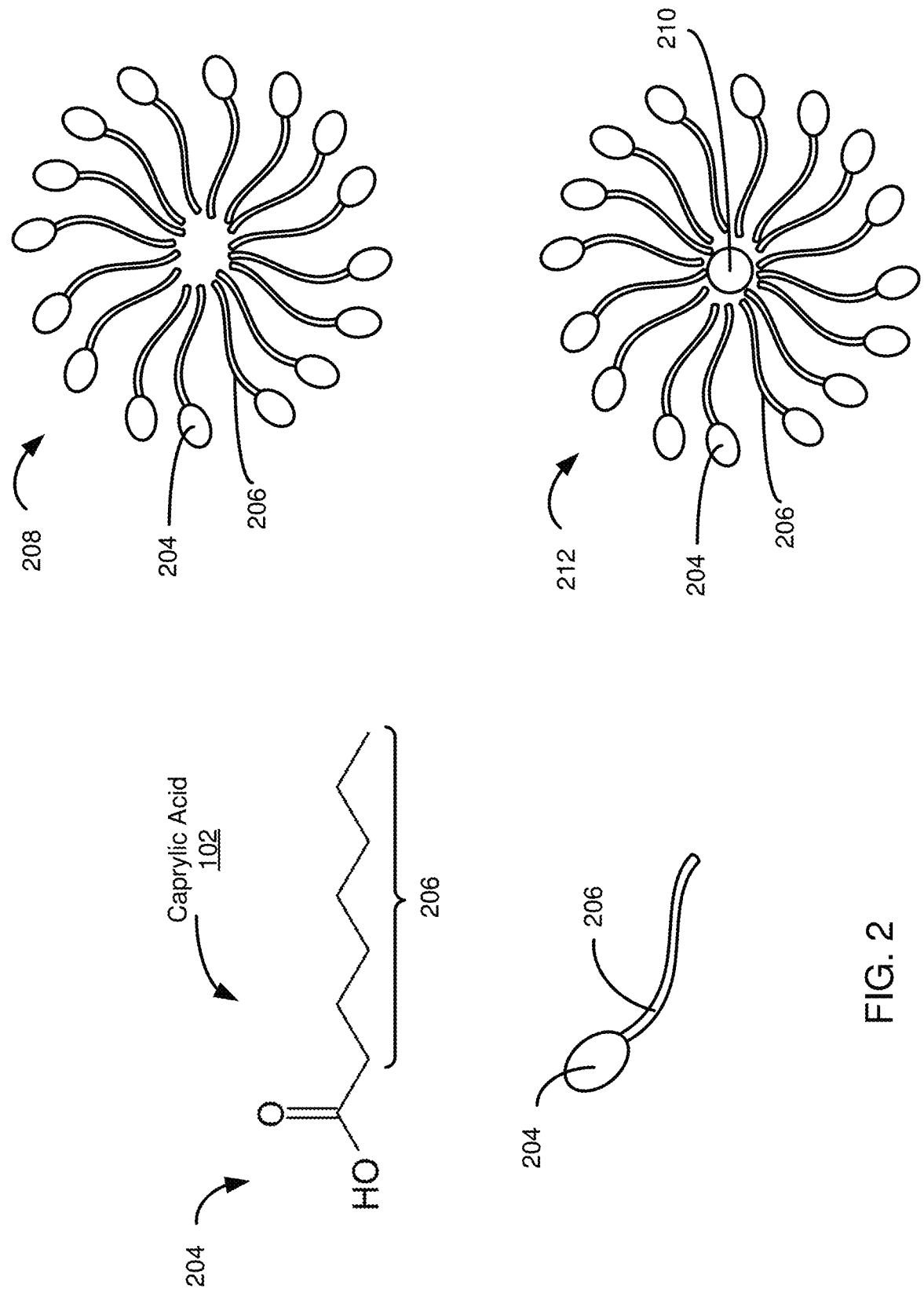
FIG. 2 is a depiction of a micellar nanostructure, according to one embodiment.

FIG. 2 illustrates a structure of a nanoparticle 208 as disclosed herein. The nanoparticle 208 includes caprylic acid 102 and an inner molecule 210. Caprylic acid 102 includes a polar group 204 and a nonpolar alkyl chain 206. The polar group 204 is the hydroxyl (OH) group at the end of the caprylic acid 102 fatty acid chain. The nonpolar alkyl chain 206 is the nonpolar carbon and hydrogen ($CH_2$) chain. The polar group 204 has a polar molecular bond such that there exist positive and negative charges within the bond. The hydrogen atom donates an electron to the oxygen atom such that the hydrogen atom has a positive charge and the oxygen atom has a negative charge within the hydroxyl (OH) bond. The nonpolar alkyl chain 206 is not polar because the electrons in the carbon-hydrogen and carbon-carbon bonds in the chain are dispersed equally. The polar group 204 is soluble in water and the nonpolar alkyl chain 206 is not soluble in water.

A plurality of the caprylic acid 102 form a caprylic acid nanostructure 208. The plurality of caprylic acid 102 molecules are situated such that the nonpolar alkyl chains 206 point to the interior of the caprylic acid nanostructure 208 and the polar group 204 heads are on the exterior of the caprylic acid nanostructure 208.

The caprylic acid nanostructure 208 forms a micellar nanostructure 212 by encapsulating an inner molecule 210 in the center of the caprylic acid nanostructure 208. The micellar nanostructure 212 can facilitate an extended release delivery of the inner molecule 210. The inner molecule 210 may include one or more molecules that may be the same or different molecules. In an embodiment, the inner molecule 210 is a volatile organic compound. In an embodiment, the inner molecule 210 an odorous compound for a fragrance such as pentyl butanoate (see 302), geraniol (see 304), vanillin (see 306), or thujone (see 308), for example.

The micellar nanostructure 212 can be implemented as a fragrance that may be used in a perfume, skin product, hair product, makeup product, and so forth. Further, the micellar nanostructure 212 can be implemented as an extended release pharmaceutical or biological compound product. The caprylic acid 102 that makes up the micellar nanostructure 212 can be food-grade such that the micellar nanostructure 212 can be safely ingested or applied topically.

Embodiments of the micellar nanostructure 212 can include solely caprylic acid 102 as shown in FIG. 2, may include a combination of caprylic acid 102 and capric acid 104, and may include capric acid 104. In an embodiment, the caprylic acid 102 is present in a range from about 30% to about 80% by weight of the total composition. In an embodiment, the capric acid 104 is present in a range from about 10% to about 60% by weight of the total composition.

Micellar nanoparticle (MNP) substances can serve as versatile delivery systems. The micellar nanostructure 212 disclosed herein that includes caprylic acid 102 and/or capric acid 104 can delivery a wide range of volatile organic compounds for a variety of purposes. The micellar nanostructure 212 can accommodate a range of inner molecules 210 that may have varying physiochemical properties.

When the micellar nanostructure 212 is implemented as an emulsion such as a lotion or other cream, the micellar nanostructure 212 can serve as an effective means for drug delivery by way of topical application. The micellar nanostructure 212 provides a means for the drug (the drug may be the inner molecule 210) to penetrate the skin and functionally create a drug depot within the stratum corneum and epidermis of the skin. This route of delivery provides advantages by avoiding contact with the gastrointestinal tract and hepatic first-pass effects. Further, this route of delivery may be more desirable or acceptable to many patients.

Drug delivery by way of the micellar nanostructure 212 disclosed herein provides a fast and inexpensive means for pharmaceutical administration. When the outer structure of the micellar nanostructure 212 includes caprylic acid 102 and/or capric acid 104 as disclosed herein, the micellar nanostructure 212 is safe for ingestion and can provide an effective means for time-delayed delivery of the inner molecule 210.

Fragrance delivery by way of the micellar nanostructure 212 disclosed herein is more effective and longer lasting when compared with traditional alcohol-based fragrance delivery solvents. The inner molecule 210 may include a volatile organic compound and specifically a molecule used for activating the olfactory system in a user. A collection of micellar nanostructures 212 may include different inner molecules 210 such that the collection of micellar nanostructures constitutes a layered fragrance with multiple scents that may serve as a perfume, skin product, hair product, air freshener, and so forth. Delivery of the fragrance by way of the micellar nanostructure 212 causes the fragrance to be released slowly over time so that the fragrance lasts longer and does not need to be applied as frequently when compared with traditional alcohol-based fragrances.

Flavor delivery by way of the micellar nanostructure 212 disclosed herein is longer lasting when compared with traditional flavor delivery systems and compositions. The inner molecule 210 may include a flavor molecule that induces a flavor or taste response in the consumer. In an implementation where it is desirable that the flavor be long lasting, such as for chewing gum or a candy, the flavor may be delivered by way of the micellar nanostructure 212 disclosed herein for longer lasting results.

The inner molecule 210 may include one or more of a wide range of molecules. FIGS. 3A-3D illustrate chemical structures of example inner molecules 210. The example molecules depicted in FIGS. 3A-3D may be particularly applicable to a fragrance implementation of the disclosure. In a fragrance implementation, the goal may be to provide an extended time release fragrance in a product such as a perfume, skin product, hair product, air freshener, makeup product, and so forth. The fragrance product will last longer and will not need to be reapplied as frequently when the fragrance molecules are delivered by way of the micellar nanostructure 212 disclosed herein.

Figure 3A:
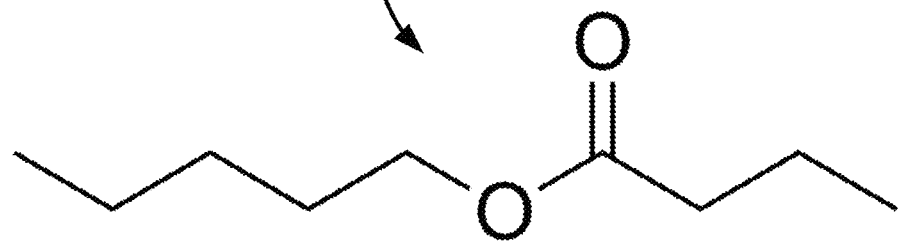
FIGS. 3A-3D are chemical structures of example volatile organic compounds suitable for use with the compositions of the disclosure.

FIG. 3A is the chemical structure of pentyl butanoate 302. Pentyl butanoate 302 is an ester. Pentyl butanoate 302 may be formed by reacting pentanol with butyric acid, usually in the presence of sulfuric acid as a catalyst. As a fragrance, pentyl butanoate 302 is known for resembling the smell of a pear or apricot and may be commonly used in sweet or fruity smelling fragrances or perfumes.

Figure 3B:
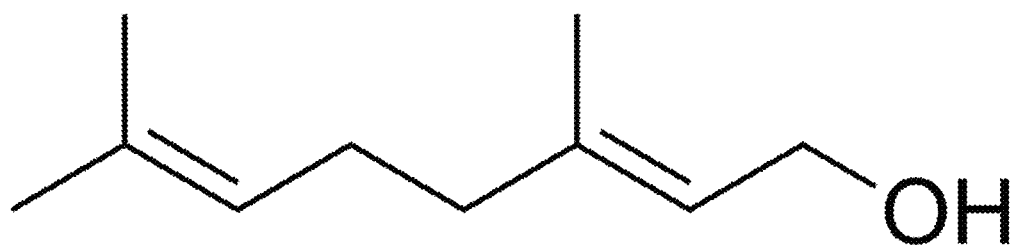

FIG. 3B is the chemical structure of geraniol 304. Geraniol 304 is a monoterpenoid and an alcohol. Geraniol 304 is the primary component of rose oil, palmarosa oil, and citronella oil. Geraniol 304 has low solubility in water. As a fragrance, geraniol 304 has a rose-like scent and is commonly used in perfumes and other fragrance products. Geraniol 304 may further be used in flavors such as peach, raspberry, grapefruit, red apple, plum, lime, orange, lemon, watermelon, pineapple, and blueberry.

Figure 3D:
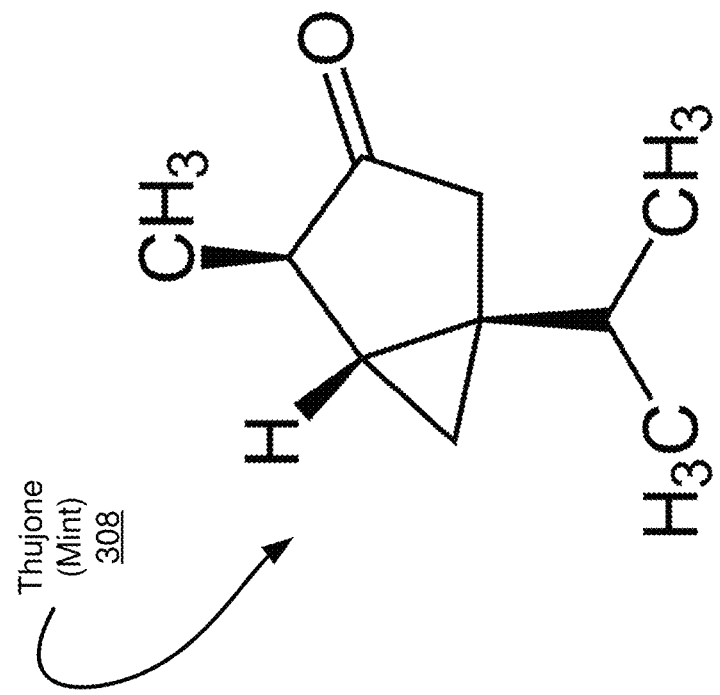
Figure 3C:
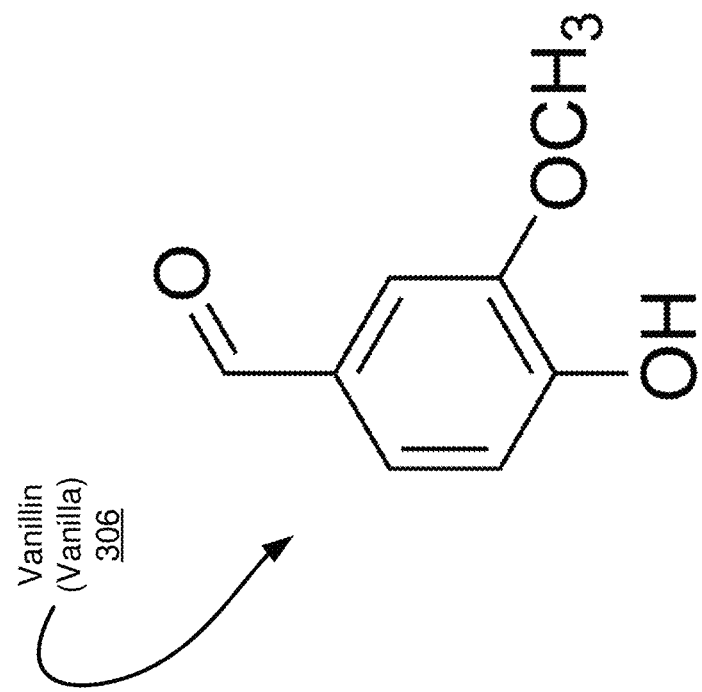

FIG. 3C is the chemical structure of vanillin 306. Vanillin 306 is an organic compound with the molecular formula $C_8H_8O_3$. Vanillin 306 is a phenolic aldehyde with functional groups including aldehyde, hydroxyl, and ether. Vanillin 306 is the primary component of the extract of the vanilla bean. Synthetic vanillin may also be manufactured and used as a vanilla extract or flavoring agent in foods, beverages, and pharmaceuticals. Artificial vanilla flavoring and artificial vanilla fragrances often include pure vanillin of a synthetic origin.

FIG. 3D is the chemical structure of thujone 308. Thujone 308 is a ketone and a monoterpene that occurs naturally in two diastereomeric forms. Thujone 308 has a menthol or minty odor. Thujone is commonly used in fragrances and perfumes, and as a component of multiple essential oils.

Figure 4:
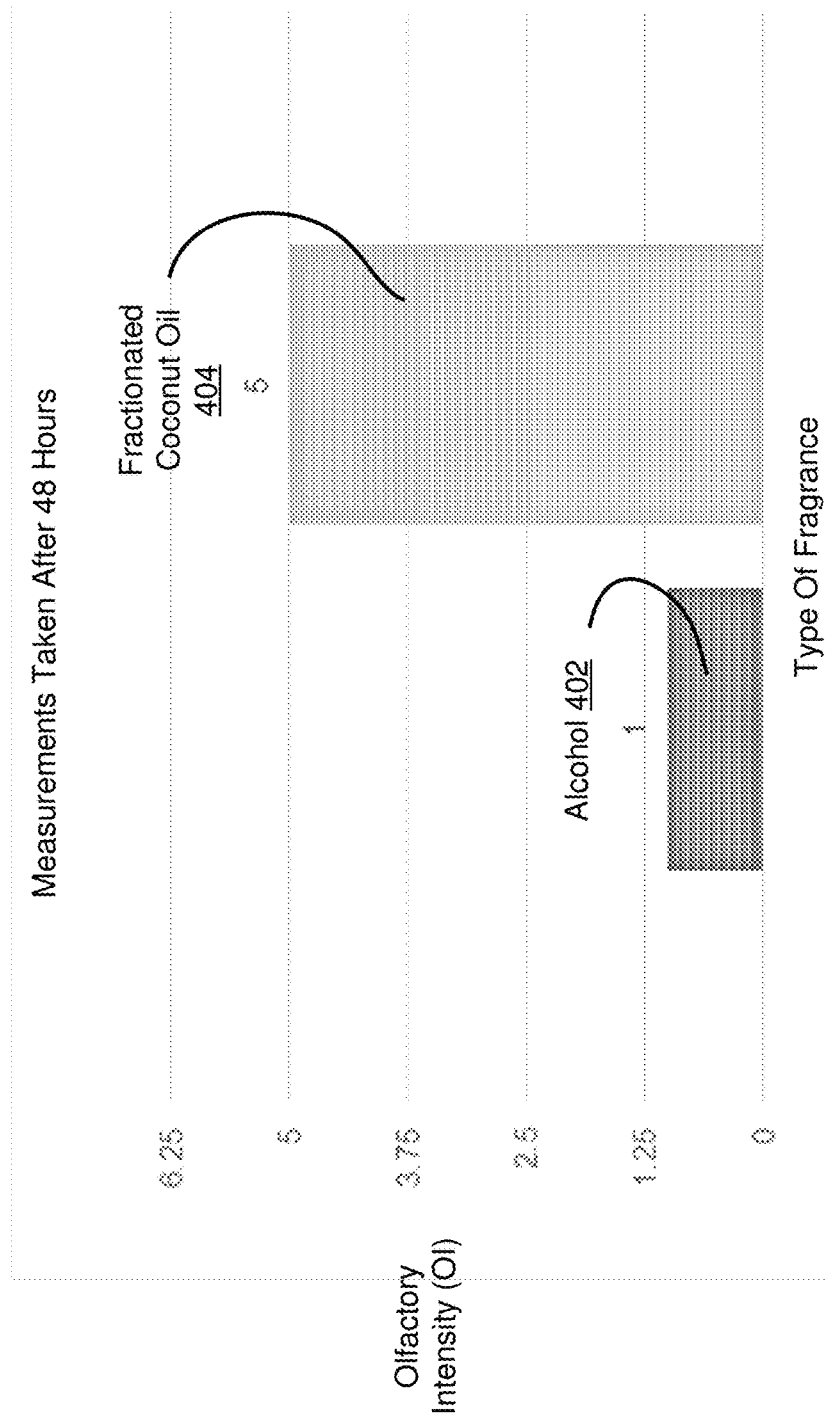
FIG. 4 is a bar graph showing the fractionated coconut oil compositions disclosed herein provide unexpectedly good results for extended time-release of volatile organic compounds.

FIG. 4 is a bar graph 400 representing the unexpectedly good fragrance retention of the composition disclosed herein. The bar graph 400 is comparison of fragrance strength between an alcohol 402 based fragrance and a fractionated coconut oil 404 fragrance made according to the methods and compositions disclosed herein. The x-axis of the bar graph 400 represents the type of fragrance measured, namely the alcohol 402 fragrance or the fractionated coconut oil 404 fragrance. The y-axis represents the strength of the fragrance in olfactory intensity (OI) as measured by subjects having rated the intensity of the fragrance on a number line from zero to five with zero meaning no detection of fragrance and five meaning very strong detection of fragrance. The measurements represented in the bar graph 400 were captured 48 hours after applying the fragrance.

In the study, two alcohol-based fragrances and two fractioned coconut oil based fragrances were used to measure the olfactory intensity of each of the four fragrances. The alcohol-based fragrances included Mankind™ by Kenneth Cole™ and CK1™ by Calvin Klein™. The fractionated coconut oil based fragrances included Cabo™ by Oligie™ and Oia™ by Oligie™ The material used in the study were 100% cotton t-shirts washed with fragrance free detergent. Each of the cotton t-shirts was sprayed with 150 μL of one of the four fragrances. Additionally, a cotton t-shirt without any fragrance was used as a control. Fragrance was applied to one set of cotton t-shirts immediately before olfactory intensity testing. Fragrance was applied to another set of cotton t-shirts 48 hours before olfactory intensity testing.

The samples of cotton t-shirts include the following: (a) control shirt with no fragrance applied; (b) cotton t-shirt with Manketh™ by Kenneth Cole™ applied immediately prior to olfactory intensity testing; (c) cotton t-shirt with Mankind™ by Kenneth Cole™ applied 48 hours before olfactory intensity testing; (d) cotton t-shirt with CK1™ by Calvin Klein™ applied immediately prior to olfactory intensity testing; (e) cotton t-shirt with CK1™ by Calvin Klein™ applied 48 hours before olfactory intensity testing; (f) cotton t-shirt with Cabo™ by Oligie™ applied immediately prior to olfactory intensity testing; (g) cotton t-shirt with Cabo™ by Oligie™ applied 48 hours before olfactory intensity testing; (h) cotton t-shirt with Oia™ by Oligie™ applied immediately prior to olfactory intensity testing; and (i) cotton t-shirt with Oia™ by Oligie™ applied 48 hours before olfactory intensity testing.

The cotton t-shirt samples were provided to subjects for the subjects to rate the olfactory intensity of each fragrance. The participants included 15 subjects including 9 female subjects and 6 male subjects. The participants did not have any known conditions of hyposmia or anosmia. The age ranges of the participants ranged from 23 to 55 years. The participants were generally in good health according to a health interview and were found to be without a cold or any sickness that might impair olfactory detection and sensitivity.

During the study, the participants were brought into a room one by one and were presented with the nine cotton t-shirt samples in randomized order. Samples were presented in a placebo controller double blind manner so that neither the subjects or the person administering the test knew the identities of each sample. Codes identifying each shirt were kept hidden from the subjects and the person administering the study. Each of the nine possible cotton t-shirt samples were presented to each participant one by one. The participants were asked to place their nose three inches above the sample and take in three deep breaths through the nose. The participants were asked to rate the intensity of the fragrance on a number line from zero to five, with give being the most intense and zero meaning no fragrance was detected. Participants took three deep breaths through the nose of a sample of coffee beans between each cotton t-shirt sample to clear the olfactory receptors of residual fragrance volatile organic compounds.

The results from the number line for each cotton t-shirt sample were collected and an average was taken between the initial intensity of the fragrance and the intensity after 48 hours for both the alcohol-based and fractionated coconut oil-based fragrances. These scores were baseline adjusted based on the intensity score given to the control cotton t-shirt.

All participants gave an olfactory intensity rating of five to both the alcohol-based and the fractionated coconut oil based fragrances that had been applied immediately prior to olfactory intensity testing. However, as shown in FIG. 4, the participants rated the fractioned coconut oil 404 based fragrances as being five times more intense than the alcohol 402 based fragrances when the fragrance had been applied 48 hours prior to olfactory intensity testing. The results shown in FIG. 4 show that there was virtually no loss in the intensity of the fractionated coconut oil 404 based fragrances 48 hours after initial application. Further, the results show that there was an 80% loss of intensity on average for the alcohol 402 based fragrances 48 hours after initial application. The results of the study attest to the sustained time release properties of combining fragrance volatile organic compounds with a fractioned coconut oil medium as taught herein.

As shown in the bar graph 400, the fragrance composition having a fractionated coconut oil 404 base shows unexpectedly good results with fragrance retention. The alcohol 402 based fragrance loses fragrance quickly, and as shown in the bar graph 400, the fragrance has mostly dissipated after 48 hours. The fragrance having a fractionated coconut oil 404 base, however, still has significant fragrance strength after 48 hours.

The bar graph 400 illustrates that the fragrance having a fractionated coconut oil 404 base demonstrates unexpectedly good results for providing an extended time-releasing effect for volatile organic compounds. While the data shown in the bar graph 400 applies to fragrance-based formulations, the same fractionated coconut oil compositions can be applied to many different implementations, including pharmaceuticals, skincare, hair care, personal care formulations, makeup products, air fresheners, and so forth.

Figure 5:
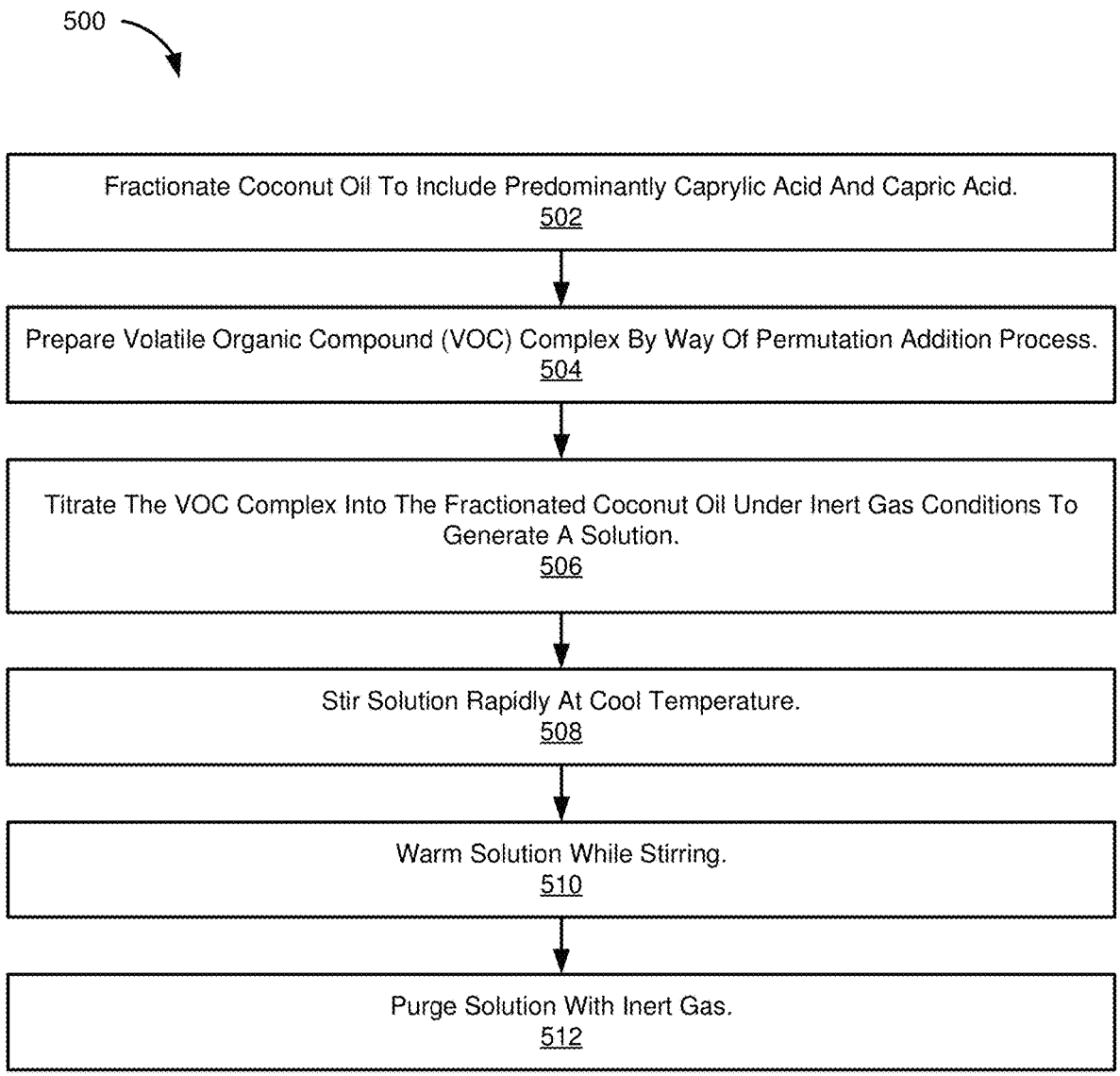
FIG. 5 is a schematic flow chart diagram of a method for manufacturing a fractionated coconut oil composition, according to one embodiment.

FIG. 5 is a block diagram of a method 500 for manufacturing a fractionated coconut oil composition as disclosed herein. The method 500 may be implemented for preparing a composition including fractionated coconut oil and a volatile organic compound. The method 500 may be implemented for preparing a fragrance that may be used as a perfume or may be incorporated into some other product such as a skincare product, a hair care product, an air freshener, a candle, and so forth. The method 500 may further be implemented for preparing a composition including fractionated coconut oil and some other inner molecule 210 such as any suitable volatile organic compound or other biological product. The method 500 may be implemented to manufacture pharmaceutical products such as topical agents, ingestible agents, and or agents that are intended to be administered by intravenously or intramuscularly.

The method 500 includes fractionating coconut oil at 502 such that the fractionated coconut oil predominantly includes caprylic acid and capric acid. In an embodiment, the fractionated coconut oil predominantly includes caprylic acid and further includes smaller amounts of capric acid. In an embodiment, lauric acid and other higher molecular weight fatty acids are largely removed from the coconut. The percentages of caprylic acid and capric acid may differ depending on the intended inner molecule 210 or volatile organic compound that will be mixed with the fractionated coconut oil. In an embodiment, the fractionated coconut oil includes caprylic acid in a concentration by weight of about 30% to about 80%. In an embodiment, the fractionated coconut oil includes capric acid in a concentration by weight of about 10% to about 60%.

The method 500 continues and includes preparing a volatile organic compound (VOC) complex at 504 by way of a permutation addition process. The VOC complex may be prepared from the permutation addition process to attain the desired overall characteristics. In an embodiment, the VOC complex is a fragrance and is prepared by the permutation addition process to attain the desired overall fragrance characteristics.

The method 500 continues and includes titrating the VOC complex into the fractionated coconut oil at 506 under inert gas conditions to generate a solution. The inert gas may include any suitable inert gas such as helium, argon, neon, xenon, krypton, and so forth. In an embodiment, the VOC complex is slowly titrated into the fractionated coconut oil while the fractionated coconut oil is being rapidly stirred. The method 500 includes stirring the solution rapidly at 508 at a cool temperature. In an embodiment, the fractionated coconut oil is stirred at a cool temperature before the VOC complex is titrated into the fractionated coconut oil, and the resulting solution continues to be stirred after titration is complete or upon completion of titration.

The method 500 continues and the solution is warmed at 510 while stirring. The solution may be stirred rapidly on a stir while the solution is heated or is allowed to warm to room temperature under ambient conditions. In an embodiment, stirring is continued when the desired warmer temperature is reached. In an embodiment, the desired warmer temperature is room temperature. The method 500 continues and the solution is purged at 512 with an inert gas. The solution may be sealed and stored at room temperature until the solution is packaged in a final container.

The compositions disclosed herein including fractionated coconut oil and one or more volatile organic compounds provide unexpectedly good results for extended time release of the one or more volatile organic compounds. The compositions disclosed herein may be manufactured according to the "like associates with like" principle of chemistry. The "like associates with like" principle means that compounds with similar structures interact with each other to form a soluble, miscible, and homogenous solution. Compounds that are not soluble with each other are immiscible or insoluble. One classic example of this principle is the immiscible solvents of oil and water. Water is a polar solvent while oil is a nonpolar solvent, and the two solvents will not mix with each other when placed in the same vessel.

In general, organic compounds such as oil are not miscible with inorganic compounds such as water. This principle has been a significant hinderance to pharmaceuticals, nutraceuticals, and cosmeceuticals. The organic bioactive compounds in such formulations will eventually come in contact with inorganic compounds such as water in the blood or on the surface of the skin. When this happens, the bioactive organic compounds exit the solution and lose the ability to exert their efficacy.

The methods of manufacture and compositions disclosed herein overcome the hurdles associated with the "like associates with like" principle of chemistry. The methods of manufacture and compositions disclosed herein generate micellar nanostructures 212 whereby organic compounds, such as volatile organic compounds, are encapsulated by other compounds. In an embodiment, one or more volatile organic compounds serve as an inner molecule 210 (or multiple inner molecules) that is encapsulated by a combination of caprylic acid 102 and capric acid 104. The caprylic acid 102 and capric acid 104 may be directly derived from coconut oil by fractionating the coconut oil to remove lauric acid and other higher molecular weight acids.

The micellar nanostructures 212 in the compositions disclosed herein are formed when amphipathic fatty acids (e.g. from the caprylic acid 102 and/or the capric acid 104) align the hydrophilic carboxylic acid function group on the outside towards water and orient the hydrophobic alkyl chain toward the inside as shown in the micellar nanostructure 212 in FIG. 2. A hydrophobic organic molecule, such as a volatile organic compound, associates with the alkyl groups inside the micellar nanostructure 212 by way of small electrostatic interactions called Van der Waals forces.

Examples

The following examples pertain to further embodiments.

According to one or more embodiments of the disclosure, a composition may include a combination of all or some, but not all, of the following ingredients:
(a) caprylic acid;
(b) capric acid; and/or
(c) volatile organic compound complex;

Other embodiments of the composition may comprise, for example, concentrations of caprylic acid as follows:
(a1) from 20% to 90% by weight the total composition;
(a2) from 20% to 85% by weight the total composition;
(a3) from 20% to 80% by weight the total composition;
(a4) from 25% to 80% by weight the total composition;
(a5) from 30% to 80% by weight the total composition;
(a6) from 32% to 80% by weight the total composition;
(a7) from 34% to 80% by weight the total composition;
(a8) from 36% to 80% by weight the total composition;
(a9) from 38% to 80% by weight the total composition;
(a10) from 40% to 80% by weight the total composition;
(a11) from 42% to 80% by weight the total composition;
(a12) from 44% to 80% by weight the total composition;
(a13) from 46% to 80% by weight the total composition;
(a14) from 48% to 80% by weight the total composition;
(a15) from 50% to 80% by weight the total composition;
(a16) from 52% to 80% by weight the total composition;
(a17) from 54% to 80% by weight the total composition;
(a18) from 56% to 80% by weight the total composition;
(a19) from 58% to 80% by weight the total composition;
(a20) from 60% to 80% by weight the total composition;
(a21) from 62% to 80% by weight the total composition;
(a22) from 64% to 80% by weight the total composition;
(a23) from 66% to 80% by weight the total composition;
(a24) from 68% to 80% by weight the total composition;
(a25) from 70% to 80% by weight the total composition;
(a26) from 72% to 80% by weight the total composition;
(a27) from 74% to 80% by weight the total composition;
(a28) from 76% to 80% by weight the total composition;
(a29) from 78% to 80% by weight the total composition;
(a30) from 30% to 78% by weight the total composition;
(a31) from 30% to 76% by weight the total composition;
(a32) from 30% to 74% by weight the total composition;
(a33) from 30% to 72% by weight the total composition;
(a34) from 30% to 70% by weight the total composition;
(a35) from 30% to 68% by weight the total composition;
(a36) from 30% to 66% by weight the total composition;
(a37) from 30% to 64% by weight the total composition;
(a38) from 30% to 62% by weight the total composition;
(a39) from 30% to 60% by weight the total composition;
(a40) from 30% to 58% by weight the total composition;
(a41) from 30% to 56% by weight the total composition;
(a42) from 30% to 54% by weight the total composition;

(a43) from 30% to 52% by weight the total composition;
(a44) from 30% to 50% by weight the total composition;
(a45) from 30% to 48% by weight the total composition;
(a46) from 30% to 46% by weight the total composition;
(a47) from 30% to 44% by weight the total composition;
(a48) from 30% to 42% by weight the total composition;
(a49) from 30% to 40% by weight the total composition;
(a50) from 30% to 38% by weight the total composition;
(a51) from 30% to 36% by weight the total composition;
(a52) from 30% to 34% by weight the total composition; or
(a53) from 30% to 32% by weight the total composition.

With respect to ingredient (a) noted above for example, the amount of caprylic acid that may be included in the final composition is based on a percent by weight of the total weight of the final composition described herein. The composition may comprise ingredient (b) for example, in concentrations as follows:

(b1) from 5% to 70% by weight the total composition;
(b2) from 5% to 65% by weight the total composition;
(b3) from 10% to 60% by weight the total composition;
(b4) from 12% to 60% by weight the total composition;
(b5) from 14% to 60% by weight the total composition;
(b6) from 16% to 60% by weight the total composition;
(b7) from 18% to 60% by weight the total composition;
(b8) from 20% to 60% by weight the total composition;
(b9) from 22% to 60% by weight the total composition;
(b10) from 24% to 60% by weight the total composition;
(b11) from 26% to 60% by weight the total composition;
(b12) from 28% to 60% by weight the total composition;
(b13) from 30% to 60% by weight the total composition;
(b14) from 32% to 60% by weight the total composition;
(b15) from 34% to 60% by weight the total composition;
(b16) from 36% to 60% by weight the total composition;
(b17) from 38% to 60% by weight the total composition;
(b18) from 40% to 60% by weight the total composition;
(b19) from 42% to 60% by weight the total composition;
(b20) from 44% to 60% by weight the total composition;
(b21) from 46% to 60% by weight the total composition;
(b22) from 48% to 60% by weight the total composition;
(b23) from 50% to 60% by weight the total composition;
(b24) from 52% to 60% by weight the total composition;
(b25) from 54% to 60% by weight the total composition;
(b26) from 56% to 60% by weight the total composition;
(b27) from 58% to 60% by weight the total composition;
(b28) from 10% to 58% by weight the total composition;
(b29) from 10% to 56% by weight the total composition;
(b30) from 10% to 54% by weight the total composition;
(b31) from 10% to 52% by weight the total composition;
(b32) from 10% to 50% by weight the total composition;
(b33) from 10% to 48% by weight the total composition;
(b34) from 10% to 46% by weight the total composition;
(b35) from 10% to 44% by weight the total composition;
(b36) from 10% to 42% by weight the total composition;
(b37) from 10% to 40% by weight the total composition;
(b38) from 10% to 38% by weight the total composition;
(b39) from 10% to 36% by weight the total composition;
(b40) from 10% to 34% by weight the total composition;
(b41) from 10% to 32% by weight the total composition;
(b42) from 10% to 30% by weight the total composition;
(b43) from 10% to 28% by weight the total composition;
(b44) from 10% to 26% by weight the total composition;
(b45) from 10% to 24% by weight the total composition;
(b46) from 10% to 22% by weight the total composition;
(b47) from 10% to 20% by weight the total composition;
(b48) from 10% to 18% by weight the total composition;
(b49) from 10% to 16% by weight the total composition;
(b50) from 10% to 14% by weight the total composition; or
(b51) from 10% to 12% by weight the total composition.

With respect to ingredient (b) noted above for example, the amount of capric acid that may be included in the final composition is based on a percent by weight of the total weight of the final composition described herein. The composition may comprise ingredient (c) for example, in concentrations as follows:

(c1) from 0.5% to 90% by weight the total composition;
(c2) from 1% to 90% by weight the total composition;
(c3) from 5% to 90% by weight the total composition;
(c4) from 10% to 90% by weight the total composition;
(c5) from 15% to 90% by weight the total composition;
(c6) from 20% to 90% by weight the total composition;
(c7) from 25% to 90% by weight the total composition;
(c8) from 30% to 90% by weight the total composition;
(c9) from 35% to 90% by weight the total composition;
(c10) from 40% to 90% by weight the total composition;
(c11) from 45% to 90% by weight the total composition;
(c12) from 50% to 90% by weight the total composition;
(c14) from 55% to 90% by weight the total composition;
(c15) from 60% to 90% by weight the total composition;
(c16) from 65% to 90% by weight the total composition;
(c17) from 70% to 90% by weight the total composition;
(c18) from 75% to 90% by weight the total composition;
(c19) from 80% to 90% by weight the total composition;
(c20) from 0.5% to 90% by weight the total composition;
(c21) from 0.5% to 85% by weight the total composition;
(c22) from 0.5% to 80% by weight the total composition;
(c23) from 0.5% to 75% by weight the total composition;
(c24) from 0.5% to 70% by weight the total composition;
(c25) from 0.5% to 65% by weight the total composition;
(c26) from 0.5% to 60% by weight the total composition;
(c27) from 0.5% to 55% by weight the total composition;
(c28) from 0.5% to 50% by weight the total composition;
(c29) from 0.5% to 45% by weight the total composition;
(c30) from 0.5% to 40% by weight the total composition;
(c31) from 0.5% to 35% by weight the total composition;
(c32) from 0.5% to 30% by weight the total composition;
(c33) from 0.5% to 25% by weight the total composition;
(c34) from 0.5% to 20% by weight the total composition;
(c35) from 0.5% to 15% by weight the total composition;
(c36) from 0.5% to 10% by weight the total composition;
(c37) from 0.5% to 9% by weight the total composition;
(c38) from 0.5% to 8% by weight the total composition;
(c39) from 0.5% to 7% by weight the total composition;
(c40) from 0.5% to 6% by weight the total composition;
(c40) from 0.5% to 5% by weight the total composition;
(c40) from 0.5% to 4% by weight the total composition;
(c40) from 0.5% to 3% by weight the total composition;
(c40) from 0.5% to 2.5% by weight the total composition;
(c40) from 0.5% to 2% by weight the total composition;
(c40) from 0.5% to 1.5% by weight the total composition; or
(c40) from 0.5% to 1% by weight the total composition.

The foregoing percentages, concentrations, and ratios are presented by example only and are not intended to be exhaustive or to limit the disclosure to the precise percentages, concentrations, and ratios disclosed. It should be appreciated that each value that falls within a disclosed range is disclosed as if it were individually disclosed as set forth herein. For example, a range indicating a weight percent from about 8% to about 14% additionally includes ranges beginning or ending with all values within that range, including for example a range beginning at 8.1%, 8.2%, 8.3%, 9%, 10%, 11%, 12%, and so forth.

Also, according to one or more non-limiting embodiments of the disclosure, any of the concentrations for ingredients (a) or (c), for example, as listed above, may indicate the concentration for ingredient (b) as listed above.

This composition may be usable as a fragrance spray, a roll on application, or may be adjusted to be implemented as a solid composition with a wax-like consistency.

Other oil based compositions may be possible. For example, sunflower oil, safflower oil, nut oils, olive oils, and other oils may be possible to use as bases in the same proportions as disclosed above (70-90%) in place of fractionated coconut oil or coconut oil.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A composition comprising:
   an effective amount of one or more volatile organic compound for providing a fragrance that can be sensed by a user;
   fractionated coconut oil comprising caprylic acid and capric acid;
   micellar nanostructures comprising at least one molecule of the one or more volatile organic compounds serving as an inner molecule and the caprylic acid and/or the capric acid serving as outer molecules surrounding the inner molecule; and
   wherein the composition is free from ethanol.

2. The composition of claim 1, wherein the fractionated coconut oil is fractionated such that lauric acid is removed.

3. The composition of claim 1, wherein the one or more volatile organic compounds comprising:
   pentyl butanoate;
   geraniol; or
   thujone.

4. The composition of claim 1, wherein the micellar nanostructures comprise at least one molecule of the effective amount of the volatile organic compound serving as an inner molecule, wherein the inner molecule is encapsulated by a plurality of outer molecules.

5. The composition of claim 4, wherein the plurality of outer molecules comprise the caprylic acid and/or the capric acid.

6. The composition of claim 1, wherein the composition is prepared by titrating the effective amount of volatile organic compound into the fractionated coconut oil under inert gas conditions.

7. The composition of claim 1, wherein the composition is prepared by mixing the effective amount of the volatile organic compound and the fractionated coconut oil to generate a solution.

8. The composition of claim 1, wherein the composition is such that the effective amount of the volatile organic compound is released over a longer period of time when compared with an alcohol-based composition comprising the effective amount of the volatile compound and an alcohol.

9. The composition of claim 1, wherein the composition is free of isopropyl alcohol.

10. The composition of claim 1, wherein the composition is prepared for one or more of:
    topical administration as an emulsion;
    topical administration as a spray;
    topical administration as a gel
    topical administration as a lotion; or
    topical administration as an ointment.

* * * * *